United States Patent [19]
Hioki et al.

[11] Patent Number: 5,912,208
[45] Date of Patent: Jun. 15, 1999

[54] AGRICULTURAL CHEMICAL COMPOSITION

[75] Inventors: Yuichi Hioki; Kazuhiko Kurita; Tadayuki Suzuki; Toshikazu Azuma, all of Wakayama, Japan

[73] Assignee: Kao Corporation, Tokyo, Japan

[21] Appl. No.: 08/912,475

[22] Filed: Aug. 18, 1997

Related U.S. Application Data

[63] Continuation of application No. 07/967,059, Oct. 28, 1992, abandoned.

[30] Foreign Application Priority Data

Oct. 31, 1991 [JP] Japan .................................. 3-286356

[51] Int. Cl.$^6$ .................................................. A01N 59/26
[52] U.S. Cl. ........................................ 504/206; 71/DIG. 1
[58] Field of Search ........................... 504/206; 71/DIG. 1

[56] References Cited

U.S. PATENT DOCUMENTS

| | | | |
|---|---|---|---|
| 3,799,758 | 3/1974 | Franz ........................................ | 504/206 |
| 3,954,977 | 5/1976 | Rife ........................................... | 424/188 |
| 4,400,196 | 8/1983 | Albrecht et al. ........................ | 504/206 |
| 4,840,942 | 6/1989 | Iwasaki et al. ......................... | 514/120 |

FOREIGN PATENT DOCUMENTS

| | | |
|---|---|---|
| 0243713 | 11/1987 | European Pat. Off. . |
| 0417896 | 3/1991 | European Pat. Off. . |
| 3523806 | 3/1987 | Germany . |
| 2080686 | 2/1982 | United Kingdom . |
| 2101487 | 1/1983 | United Kingdom . |

OTHER PUBLICATIONS

Chemical Abstracts (1986), vol. 104(21), Abstract No. 181762j.
Chemical Patents Index, Section Ch, Week 3948, 31 Jan. 1990, & JP–A–01 261 304 (AN 351365) Documentation Abstracts Journal.
Chemical Abstracts, vol. 104, No. 21, 26 May 1986, abst. No. 181762j, & JP–A–60 224 602.
Chemical Abstracts, vol. 98, No. 25, 20 Jun. 1983, abstract No. 214781c, & AU–A–515 436.
Chemical Patents Index, Documentation Abstracts Journal, Sec. Ch, Week 9109, 13 Mar. 1991, & JP–A–02 286 608 (AN 312192).
Chemical Patents Index, Basic Abstracts Journal, Sec. Ch, Week 3830, 21 Sep. 1998, AN 209819 & JP–A–63 146 804.
Chemical Patents Index, Basic Abstracts Journal, Sec. Ch, Week 3812, 18 May. 1988, AN 080715 & JP–A–63 033 305.
Chemical Abstracts, vol. 108, No. 19, 9 May 1988, abstract No. 166364v, & JP–A–62 148 424.
Chemical Abstracts, vol. 95, No. 13, 23 Sep. 1981, abstract No. 110151u, & JP–A–81 043 207.
McCutcheon's vol. 1 Emulsifiers & Detergents, 1990 International Edition, p. 100.

*Primary Examiner*—Deborah C. Lambkin
*Attorney, Agent, or Firm*—Birch, Stewart, Kolasch & Birch, LLP

[57] ABSTRACT

An agricultural chemical composition which can be safely applied to crops without causing any chemical damage comprising a mixture, which exerts excellent potentiating effects on various agricultural chemicals and has n of from 2 to 50 on the average and x1+y1+z1+x2+y2+z2+x3+y3+z3 of from 0 to 100 on the average, of compounds represented by the following general formula (I) and an agricultural chemical, wherein the weight ratio of the mixture to the agricultural chemical ranges from 0.1 to 20:

$$R^1O-(EO)_{x1}(PO)_{y1}(BO)_{z1}-(CH_2CHCH_2O)_n-(EO)_{x3}(PO)_{y3}(BO)_{z3}-R^3 \quad \text{(I)}$$
$$\underset{|}{(EO)_{x2}(PO)_{y2}(BO)_{z2}-OR^2}$$

wherein $R^1$, $R^2$ and $R^3$ each represent a hydrogen atom or an acyl group having from 2 to 31 carbon atoms, $-SO_3Na$, $-SO_3K$, $-SO_3H \cdot N(C_2H_4OH)_3$ or $-SO_3H \cdot NH(C_2H_4OH)_2$;

$(EO)_{x1}$, $(EO)_{x2}$ and $(EO)_{x3}$ each represent a polyoxyethylene chain;

$(PO)_{y1}$, $(PO)_{y2}$ and $(PO)_{y3}$ each represent a polyoxypropylene chain;

$(BO)_{z1}$, $(BO)_{z2}$ and $(BO)_{z3}$ each represent a polyoxybutylene chain;

n represents an integer of 1 or more;

x1, y1, z1, x2, y2, z2, x3, y3 and z3 each represent 0 or an integer of 1 or more;

x1+y1+z1, x2+y2+z2 and x3+y3+z3 each represent 0 or an integer of 1 to 200; and x1+y1+z1+x2+y2+z2+x3+y3+z3 represents 0 or an integer of 1 to 600.

17 Claims, No Drawings

AGRICULTURAL CHEMICAL COMPOSITION

This application is a continuation of application Ser. No. 07/967,059 filed on Oct. 28, 1992, now abandoned.

BACKGROUND OF THE INVENTION

1. Field of the Invention

The present invention relates to a novel agricultural chemical composition.

2. Description of the Related Art

Agricultural chemical compositions such as insecticide compositions, bactericide compositions, herbicide compositions, miticide compositions and plant growth regulator compositions have been used in various forms, for example, emulsions, wettable powders, granules, dusts or flowables. In the preparation of these agricultural chemical compositions, various attempts have been made to make good use of the efficacy of the agricultural chemicals, but it has been found to be difficult under current circumstances to further potentiate the agricultural chemicals through formulated contrivances. Further, it is difficult to develop various novel active ingredients for agricultural chemical compositions. Thus it is highly important from an industrial viewpoint to further potentiate the existing agricultural chemicals.

In the field of agricultural chemicals, it has been known that moisture plays an important role in the surface absorption of agricultural chemicals and that the content of retained water is increased by using a humectant. This seemingly suggests that humectants such as glycerol, ethylene glycol and propylene glycol could potentiate agricultural chemicals.

Japanese Patent Publication-A Nos. 146804/1988 (published on Jun. 18, 1988) and 33305/1988 (published on Feb. 13, 1988) disclosed an agricultural chemical composition containing, as a stabilizer, at least one compound selected from the group consisting of glycerol, polyglycerol, ethylene glycol, polyethylene glycol, propylene glycol, polypropylene glycol, polyoxyethyleneoxypropylene glycol, polyoxyethyleneoxybutylene glycol and polyoxyethyleneoxypropyleneoxybutylene glycol.

U.S. Pat. No. 4,868,217 (pulished on Sep. 19, 1989; Eisai Co., Ltd. and Kao Corporation) disclosed a bactericide composition containing an alkylene oxide adduct of a polyfunctional alcohol having tri- or more functional groups.

Japanese Patent Publication-A No. 286608/1990 (published on Nov. 26, 1990) disclosed a bactericide composition containing a (poly)glycerol fatty acid ester.

Furthermore, U.S. Pat. No. 4,840,942 (pulished on Jun. 20, 1989; Kao Corporation) disclosed an agricultural biocidal composition containing an emulsifier comprising a nonionic surfactant of the formula: $R^1-Y^1-(R^3O)_n-Y^2-R^2$ (wherein $R^1$ and $R^2$ are each a saturated or ethylenically unsaturated hydrocarbon group, with the proviso that at least one of $R^1$ and $R^2$ has at least 8 carbon atoms, $Y^1$ is —COO— or —O—, $Y^2$ is —OC— or represents a direct valence bond between $(R^3O)_n$ and $R^2$, $R^3$ is $C_2$-$C_4$ alkylene, and n is an integer of from 1 to 100).

DISCLOSURE OF THE INVENTION

Summary of the Invention

From the viewpoint that the above-described humectants, stabilizers, emulsifiers, etc. can potentiate agricultural chemicals, the present inventors have conducted extensive studies. As a result, they have found that a polyglycerol or a polyglycerol derivative is superior to common humectants in the ability to potentiate various agricultural chemicals, thus completing the present invention.

Accordingly, the present invention provides an agricultural chemical composition (1) comprising or consisting essentially of a mixture of compounds represented by the following general formula (I) which has n of from 2 to 50 on the average and x1+y1+z1+x2+y2+z2+x3+y3+z3 of from 0 to 100 on the average, and an agricultural chemical, wherein the weight ratio of the mixture to the agricultural chemical ranges from 0.1 to 20:

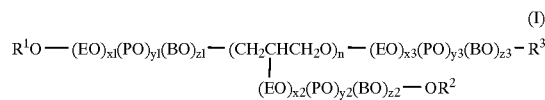

wherein $R^1$, $R^2$ and $R^3$ each represent a hydrogen atom, an acyl group having from 2 to 31 carbon atoms, —$SO_3Na$, —$SO_3K$, —$SO_3H \cdot N(C_2H_4OH)_3$ or —$SO_3H \cdot NH(C_2H_4OH)_2$;

$(EO)_{x1}$, $(EO)_{x2}$ and $(EO)_{x3}$ each represent a polyoxyethylene chain;

$(PO)_{y1}$, $(PO)_{y2}$ and $(PO)_{y3}$ each represent a polyoxypropylene chain;

$(BO)_{z1}$, $(BO)_{z2}$ and $(BO)_{z3}$ each represent a polyoxybutylene chain;

n represents an integer of 1 or more;

x1, y1, z1, x2, y2, z2, x3, y3 and z3 each represent 0 or an integer of 1 or more;

x1+y1+z1, x2+y2+z2 and x3+y3+z3 each represent 0 or an integer of 1 to 200; and x1+y1+z1+x2+y2+z2+x3+y3+z3 represents 0 or an integer of 1 to 600.

The agricultural chemical means those materials which are employed as active ingredients for common agricultural chemical compositions, such as active ingredients of bactericides, insecticides, miticides, herbicides, plant growth regulators, etc., an agricultural medicine, a biocide, a matter being effective for an agricultural medicine or an agricultural medicine base.

The above-described present invention includes an agricultural chemical composition comprising a polyglycerol and/or a polyglycerol derivative represented by the following general formula (II) and an agricultural chemical, wherein the weight ratio of the polyglycerol and/or the polyglycerol derivative to the agricultural chemical ranges from 0.1 to 20:

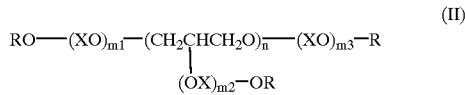

wherein n represents a number of from 2 to 50;

R represents a hydrogen atom or an acyl group having from 2 to 31 carbon atoms;

X represents an alkylene group having from 2 to 4 carbon atoms; and $m_1$, $m_2$ and $m_3$ represent each a number of from 0 to 200.

The present invention also provides an agricultural chemical composition (2) comprising or consisting essentially of a mixture of compounds represented by the above general formula (I) which has n of from 2 to 50 on the average and $x1+y1+z1+x2+y2+z2+x3+y3+z3$ of from 0 to 100 on the average and a surfactant other than the compounds represented by the above general formula (I) as the adjuvants, and an agricultural chemical, wherein the weight ratio of the total amount of the adjuvants to the agricultural chemical ranges from 0.1 to 20.

The above-described present invention includes an agricultural chemical composition comprising a polyglycerol and/or a polyglycerol derivative represented by the above general formula (II) and a surfactant as the adjuvants and an agricultural chemical, wherein the weight ratio of the adjuvants to the agricultural chemical ranges from 0.1 to 20.

The present invention further provides a kit (1) comprising or consisting essentially of package (A) comprising or consisting essentially of a mixture of compounds represented by the above general formula (I) which has n of from 2 to 50 on the average and $x1+y1+z1+x2+y2+z2+x3+y3+z3$ of from 0 to 100 on the average and package (B) comprising or consisting essentially of an agricultural chemical, wherein the weight ratio of the mixture to the agricultural chemical ranges from 0.1 to 20; a kit (2) comprising or consisting essentially of package (A) comprising or consisting essentially of a mixture of compounds represented by the above general formula (I) which has n of from 2 to 50 on the average and $x1+y1+z1+x2+y2+z2+x3+y3+z3$ of from 0 to 100 on the average, package (C) comprising or consisting essentially of a surfactant other than the compounds represented by the above general formula (I) and package (B) comprising or consisting essentially of an agricultural chemical, wherein the weight ratio of the total amount of the mixture and the surfactant to the agricultural chemical ranges from 0.1 to 20; and a kit (3) comprising or consisting essentially of package (D) comprising or consisting essentially of a mixture of compounds represented by the above general formula (I) which has n of from 2 to 50 on the average and $x1+y1+z1+x2+y2+z2+x3+y3+z3$ of from 0 to 100 on the average and a surfactant other than the compounds represented by the above general formula (I) and package (B) comprising an agricultural chemical, wherein the weight ratio of the total amount of the mixture and the surfactant to the agricultural chemical ranges from 0.1 to 20.

The present invention provides a bactericidal, insecticidal, miticidal, herbicidal or plant growth regulating method (1), wherein an agricultural chemical composition (3) comprising from 0.02 to 8% by weight of a mixture of compounds represented by the above general formula (I) which has n of from 2 to 50 on the average and $x1+y1+z1+x2+y2+z2+x3+y3+z3$ of from 0 to 100 on the average and an agricultural chemical which is present in an amount of from 0.1 to 50 times as much as the mixture, is employed, and a bactericidal, insecticidal, miticidal, herbicidal or plant growth regulating method (2), wherein an agricultural chemical composition (4) comprising from 0.02 to 8% by weight of adjuvants comprising or consisting essentially of a mixture of compounds represented by the above general formula (I) which has n of from 2 to 50 on the average and $x1+y1+z1+x2+y2+z2+x3+y3+z3$ of from 0 to 100 on the average and a surfactant other than the compounds represented by the above general formula (I), and an agricultural chemical which is present in an amount of from 0.1 to 50 times as much as the total amount of the adjuvants, is employed.

Further scope and the applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

In the present invention, a mixture consisting essentially of compounds represented by the above-mentioned general formula (I) and having n of from 2 to 50 on the average and $x1+y1+z1+x2+y2+z2+x3+y3+z3$ of from 0 to 100 on the average is used as an adjuvant. Namely, a mixture of compounds represented by the above general formula (I), which differ from each other by at least one of $R^1$, $R^2$, $R^3$, n, x1, x2, x3, y1, y2, y3, z1, z2 and z3 is employed. Certainly, a mixture comprising two or more of the above-described mixtures may be used.

The compounds represented by the above general formula (I) include polyglycerols, mono- or polyesters of polyglycerol with a fatty acid(s), mono- or polyesters of polyglycerol with a sulfuric acid salt(s), alkylene oxide adducts of polyglycerol, alkylene oxide adducts of mono- or polyester of polyglycerol with a fatty acid(s), alkylene oxide adducts of mono- or polyesters of polyglycerol with a sulfuric acid salt(s).

In the above general formula (I), each of $R^1$, $R^2$ and $R^3$ represent a hydrogen atom, an acyl group having from 2 to 31 carbon atoms, $-SO_3Na$, $-SO_3K$, $-SO_3H.N(C_2H_4OH)_3$ or $-SO_3H.NH(C_2H_4OH)_2$. The acyl group represents formula R'CO— (wherein R' is selected from among, for example, an alkyl group, an alkenyl group or a hydroxyalkyl group having from 1 to 30 carbon atoms which may be branched). Each of the $R^1$, $R^2$ and $R_3$ in the general formula (I) may be derived from a condensed (hydroxy) carboxylic acid with a degree of condensation of from 2 to 20.

N in the above general formula (I) represents the degree of polymerization of glycerol and is an integer of 1 or more.

In the above general formula (I), $(EO)_{x1}$, $(EO)_{x2}$ and $(EO)_{x3}$ each represent a polyoxyethylene chain; $(PO)_{y1}$, $(PO)_{y2}$ and $(PO)_{y3}$ each represent a polyoxypropylene chain; and $(BO)_{z1}$, $(BO)_{z2}$ and $(BO)_{z3}$ each represent a polyoxybutylene chain. Either one of these alkylene oxides or two or more of them may be added in block or in random. In the general formula (I), x1, y1, z1, x2, y2, z2, x3, y3 and z3 each represent 0 or an integer of 1 or more, preferably 0 or an integer of 1 to 30; $x1+y1+z1$, $x2+y2+z2$ and $x3+y3+z3$ each represent 0 or an integer of 1 to 200, preferably 0 or an integer of 1 to 90; and $x1+y1+z1+x2+y2+z2+x3+y3+z3$ represents 0 or an integer of 1 to 600, preferably 0 or an integer of 1 to 200. Further, $x1+x2+x3$, $y1+y2+y3$ and $z1+z2+z3$ each represent preferably an integer of 1 to 200, still preferably an integer of 1 to 100.

In the present invention, a mixture consisting essentially of compounds represented by the above general formula (I) and having n of from 2 to 50 on the average, preferably from 2 to 15 on the average and $x1+y1+z1+x2+y2+z2+x3+y3+z3$ of from 0 to 100 on the average, preferably from 0 to 25 on the average is used as an adjuvant.

When the average degree of polymerization ($\bar{n}$) is below 2, the dispersibility of the agricultural chemical in the agricultural chemical composition deteriorates. On the other hand, when $\bar{n}$ exceeds 50, the production of the mixture according to the present invention is not economical.

When the average of $x1+y1+z1+x2+y2+z2+x3+y3+z3$, i.e., $\overline{x1+y1+z1+x2+y2+z2+x3+y3+z3}$, exceeds 100, the production of the mixture according to the present invention is not economical. Additionally, the mixture which has the average of x1+y1+z1+x2+y2+z2+x3+y3+z3 of more than 100 shows a low potentiating effect of agricultural chemicals because it has a low surface activity.

The average number of moles of the ethylene oxide added ($\overline{x1+x2+x3}$), to the compounds constituting the mixture according to the present invention, is taken as the number of moles of ethylene oxide added to the mixture; the average number of moles of the propylene oxide added ($\overline{y1+y2+y3}$), to the compounds constituting the mixture, is taken as the number of moles of propylene oxide added to the mixture, and the average number of moles of the butylene oxide added ($\overline{z1+z2+z3}$), to the compounds constituting the mixture, is taken as the number of moles of butylene oxide added to the mixture. In the present invention, $\overline{x1+x2+x3}$, $\overline{y1+y2+y3}$ and $\overline{z1+z2+z3}$ each represent preferably 1 to 100.

In the present invention, a mixture of polyglycerol derivative (mono- or polyesters of polyglycerol, alkylene oxide adducts of polyglycerol and alkylene oxide adducts of mono- or polyester of polyglycerol), i.e., mixture (a) of compounds represented by the general formula (I) which has n of from 2 to 50 on the average and x1+y1+z1+x2+y2+z2+x3+y3+z3 of from 1 to 100 on the average or mixture (b) of compounds represented by the following general formula (I') which has n of from 2 to 50 on the average, is preferably employed:

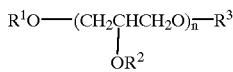
(I')

wherein $R^1$, $R^2$ and $R^3$ each represent a hydrogen atom, an acyl group having from 2 to 31 carbon atoms, —SO$_3$Na, —SO$_3$K, —SO$_3$H.N(C$_2$H$_4$OH)$_3$ or —SO$_3$H.NH(C$_2$H$_4$OH)$_2$ provided that at least one of $R^1$, $R^2$ and $R^3$ represent an acyl group having from 2 to 31 carbon atoms, —SO$_3$Na, —SO$_3$K, —SO$_3$H.N(C$_2$H$_4$OH)$_3$ or —SO$_3$H.NH(C$_2$H$_4$OH)$_2$; and n represents an integer of 1 or more.

Mixture (c), which is a mixture of compounds represented by the above general formula (I') provided that at least one of $R^1$, $R^2$ and $R^3$ represent —SO$_3$Na, —SO$_3$K, —SO$_3$H.N(C$_2$H$_4$OH)$_3$ or —SO$_3$H.NH(C$_2$H$_4$OH)$_2$ and having n of from 2 to 50 on the average, is more preferable.

Furthermore, mixture (d), which is a mixture of compounds represented by the following general formula (I") and having n of from 2 to 50 on the average and x1+y1+z1+x2+y2+z2+x3+y3+z3 of from 1 to 100 on the average, is also more preferable:

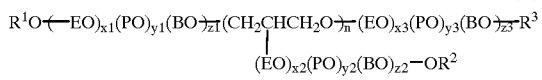
(I")

wherein $R^1$, $R^2$ and $R^3$ each represent a hydrogen atom, an acyl group having from 2 to 31 carbon atoms, —SO$_3$Na, —SO$_3$K, —SO$_3$H.N(C$_2$H$_4$OH)$_3$ or —SO$_3$H.NH(C$_2$H$_4$OH)$_2$ except that $R^1$, $R^2$ and $R^3$ represent hydrogen atoms simultaneously and that $R^1$, $R^2$ and $R^3$ represent acyl groups having from 2 to 31 carbon atoms simultaneously;

(EO)$_{x1}$, (EO)$_{x2}$ and (EO)$_{x3}$ each represent a polyoxyethylene chain;

(PO)$_{y1}$, (PO)$_{y2}$ and (PO)$_{y3}$ each represent a polyoxypropylene chain;

(BO)$_{z1}$, (BO)$_{z2}$ and (BO)$_{z3}$ each represent a polyoxybutylene chain;

n represents an integer of 1 or more;

x1, y1, z1, x2, y2, z2, x3, y3 and z3 each represent 0 or an integer of 1 or more;

x1+y1+z1, x2+y2+z2 and x3+y3+z3 each represent 0 or an integer of 1 to 200; and x1+y1+z1+x2+y2+z2+x3+y3+z3 represents 0 or an integer of 1 to 600.

The mixture consisting essentially of compounds represented by the above general formula (I), i. e., a mixture of polyglycerols or a mixture of polyglycerol derivatives to be used in the present invention may be obtained by any commonly known method.

For example, polyglycerol may be synthesized by a method which is employed on an industrial scale at present and comprises dehydrating and condensing glycerol at a temperature as high as from 200 to 300° C in the presence of an alkali catalyst.

Examples of the alkali catalyst include NaOH, KOH, LiOH, Na$_2$CO$_3$, K$_2$CO$_3$, Li$_2$CO$_3$, CaO and MgO. Although the degree of polymerization may be controlled by varying the reaction conditions, the product thus obtained is not a single compound but a mixture having a certain molecular weight distribution. For example, a commercially available product called "hexaglycerol" consists of polyglycerols of various degrees of polymerization and glycerol as the case may be, though its hydroxyl value agrees with the theoretical value.

The mixture of polyglycerols thus obtained is in the form of a yellow to dark brown liquid having a high viscosity. The hue of the mixture of polyglycerols is worsened (i.e., darkened) as the degree of polymerization is elevated. It is a practice to decolor or bleach the mixture of polyglycerols by treating it with an adsorbent such as active carbon or active clay. Or alternatively, it is a practice to remove the catalyst from the mixture of polyglycerols and to decolor or bleach the mixture with the use of an ion exchange resin. There are marketed di-, tetra-, hexa- and decaglycerols, i.e., a mixture of polyglycerols ($\overline{n}$=2, 4, 6 or 10) in general.

The mixture of alkylene oxide adducts of polyglycerol to be used in the present invention is produced by, for example, a known method which comprises adding an alkali catalyst to the mixture of polyglycerols obtained above and conducting an addition reaction with an alkylene oxide under an elevated pressure at an elevated temperature. Examples of the alkylene oxide to be added involve those having from 2 to 4 carbon atoms, i. e., ethylene oxide, propylene oxide and butylene oxide. Either one of these alkylene oxides or two or more of them may be added in block or at random.

A mixture of polyglycerol/fatty acid esters which is a mixture consisting essentially of compounds represented by the above general formula (I) according to the present invention, is produced through direct esterification of a mixture of polyglycerols. A number of esters including hydrophilic and lipophilic esters can be produced by appropriately combining mixtures of polyglycerols having various average degrees of polymerization, various fatty acids and various degrees of esterification. Thus a mixture of esters having a desired hydrophilic-lipophilic balance (HLB) can be produced.

The esterification may be effected at a temperature of 200° C. or above without using any catalyst or in the presence of an alkali catalyst. Means for obtaining a product excellent in hue and odor include the addition of a sulfite to the reaction mixture during the reaction, the use of a fatty acid having a high heat stability, and the use of lipase in the synthesis, and products of various degrees of purification are commercially available depending on the purpose. In order to obtain a mixture of fatty acid esters of polyglycerols of excellent qualities, it is essential to use a mixture of polyglycerols of good quality. This need increases particularly when, as a product, a mixture comprising fatty acid esters of polyglycerols having a higher degree of polymerization is desired. Since the qualities of the mixture of esters largely depend on the qualities of a mixture of polyglycerols, a mixture of polyglycerols should be sufficiently purified.

A polyglycerol/condensed ricinoleic acid ester, i.e., a mixture of condensed ricinoleic acid esters of polyglycerols, is synthesized by precondensing ricinoleic acid (castor oil fatty acid) by dehydration with heating for 3 to 6 minutes and then esterifying the product with a mixture of polyglycerols. The reaction conditions therefor are almost the same as those employed for producing a mixture of polyglycerol fatty acid esters.

A mixture of polyglycerol/sulfuric acid salt esters, i.e., a mixture of compounds represented by the general formula (I) provided that at least one of $R^1$, $R^2$ and $R^3$ represent —$SO_3Na$, —$SO_3K$, —$SO_3H.N(C_2H_4OH)_3$ or —$SO_3H.NH(C_2H_4OH)_2$, can also be produced through direct esterification method, and a mixture of polyglycerol/sulfuric acid salt esters having a desired hydrophilic-lipophilic balance (HLB) can be obtained.

Further, esterification similar to that mentioned above may be carried out by using a mixture of polyglycerol/alkylene oxide adducts as a starting material. Alternately, an alkylene oxide may be added to a mixture of fatty acid esters of polyglycerols or a mixture of esters of a sulfuric acid salt with polyglycerols in the presence of an alkali catalyst at a high temperature under an elevated pressure. Examples of the alkylene oxide which can be added include ethylene oxide, propylene oxide and butylene oxide. Either one of these alkylene oxides or two or more of them may be added in block or at random.

When used together with an agricultural chemical, the mixture comprising compounds represented by the above general formula (I) as an adjuvant can enhance the effects of the agricultural chemical without causing any chemical damage.

It is not necessarily evident why the mixture comprising compounds represented by the above general formula (I) according to the present invention has the remarkable effect of potentiating any agricultural chemicals used in agricultural chemical compositions, irrespective of their structure. It is conceivable, however, that one reason therefor may reside in the fact that the mixture according to the present invention has such a potent power of solubilizing the agricultural chemical used in the agricultural chemical composition that the agricultural chemical becomes finely grained, thus promoting the diffusion of the agricultural chemical on a surface of a plant, an insect or a bacterial cell thus facilitating the permeation of the agricultural chemical into the plant, insect or bacterial cell.

When the mixture comprising compounds represented by the general formula (I) according to the present invention is used together with a surfactant other than the compounds represented by the general formula (I), the amount of the mixture can be reduced and the stability of the agricultural chemical composition can be increased while the potentiating effect of the mixture to the agricultural chemical is maintained. Examples of the surfactant usable herein as an adjuvant include nonionic, anionic, cationic and amphoteric surfactants, and mixtures thereof.

Examples of the nonionic surfactants include polyoxyethylene alkyl ethers, polyoxyethylene alkylaryl ethers, polyoxyethylene alkylaryl ether/formaldehyde condensates, polyoxyalkylene aryl ethers, polyoxyalkylene alkyl esters, polyoxyalkylene alkyl sorbitol esters, polyoxyalkylene sorbitan esters, polyoxyalkylene alkyl glycerol esters, polyoxyalkylene block copolymers, polyoxyalkylene block copolymer alkylglycerol esters, polyoxyalkylene alkyl sulfonamides, polyoxyalkylene rosin esters, polyoxypropylene block copolymers, polyoxyethylene oleyl ethers, polyoxyalkylene alkylphenols and mixtures consisting of two or more of these substances.

Examples of the cationic surfactants include polyoxyalkylamines such as ethoxylated tallow amine, ethoxylated oleylamine, ethoxylated soy amine, ethoxylated coco amine, ethoxylated synthetic alkylamine and ethoxylated octylamine and mixtures consisting of two or more of these substances.

Examples of the anionic surfactants, which are typically available in the form of an aqueous solution or a solid, include sodium aryl sulfate, sodium mono- or di-alkylnapthalenesulfonates, sodium α-oleinsulfonate, sodium alkanesulfonate, alkyl sulfates, polyoxyalkylene alkyl ether sulfonates, polyoxyalkylene alkylaryl ether sulfates, polyoxyalkylene styrylphenyl ether sulfates, mono- or di-alkylbenzenesulfonates, alkylnapthalenesulfonates, alkylnaphthalenesulfonate/formaldehyde condensates, alkyl diphenyl ether sulfonates, olefinic-sulfonates, alkyl phosphates, polyoxyalkylene alkyl phosphates, polyoxyalkylene phenyl ether phosphates, polyoxyalkylphenol phosphates, polycarboxylic acid salts, fatty acid salts, stearic acid and its salts, oleic acid and its salts, N-methyl fatty acid taurides and mixtures consisting of two or more compounds selected from among those cited above, involving sodium, potassium, ammonium and amine salts.

Examples of suitable amphoteric surfactants include lauryldimethylamine oxide, Armox C mfd. by Lion Co., Ltd., Catinal mfd. by Toho Chemical Co., Ltd., Amphitol 24B mfd. by Kao Corporation, betaines, other amine oxides and mixtures consisting of two or more substances selected from among those cited above.

Among these surfactants, nonionic surfactants are particularly preferable. It is still preferable to use ester-type surfactants such as polyoxyalkylene sorbitan esters and polyoxyalkylene alkyl glycerol esters; polyoxyalkylene alkyl ethers and polyoxyalkylene alkylnonylphenols.

Although the ratio of the mixture comprising compounds represented by the general formula (I) to the surfactant other than the compounds represented by the general formula (I) in the agricultural chemical composition (2) is not particularly restricted, the weight ratio of the surfactant to the mixture may range from 0(excluded)/100 to 50/50, preferably from 10/90 to 40/60. When the surfactant is used in an amount exceeding the ratio as defined above, the potentiating effect of the adjuvants deteriorates, and thus the obtained adjuvant composition, which contains a mixture of compounds represented by the general formula (I) and a surfactant other than the compounds represented by the general formula (I), is not practically usable. In this case, however, a satisfactory effect can be achieved by increasing the amount of the mixture comprising compounds represented by the general formula (I).

The agricultural chemical composition (1) of the present invention comprises a mixture comprising compounds represented by the general formula (I) as an adjuvant and an agricultural chemical. It is necessary for the agricultural chemical composition (1) of the present invention to have a weight ratio of the adjuvant to the agricultural chemical within a range of from 0.1 to 50, preferably from 0.1 to 10.

When this weight ratio is below 0.1, no satisfactory effect can be achieved. When this ratio exceeds 50, on the other hand, the effect cannot be further improved.

The agricultural chemical composition (2) of the present invention comprises a mixture comprising compounds represented by the general formula (I) and a surfactant other than the compounds represented by the general formula (I) as adjuvants and an agricultural chemical. It is necessary for the agricultural chemical composition (2) of the present invention to have a weight ratio of the total amount of the adjuvants to the agricultural chemical within a range of from 0.1 to 50, preferably from 0.1 to 10. When this weight ratio is below 0.1, no satisfactory effect can be achieved. When this ratio exceeds 50, on the other hand, the effect cannot be further improved.

The adjuvant(s) according to the present invention can be safely applied to various crops without causing any chemical damage.

The agricultural chemical compositions (1) and (2) of the present invention may be in any form, for example, an emulsion, a wettable powder, a granule, a flowable powder, a dust or the like without restriction. Thus, the agricultural chemical compositions (1) and (2) according to the present invention may further contain other additives such as emulsifiers, dispersing agents and supports depending on the form of preparation.

Now, the agricultural chemicals, i.e., active ingredients used for agricultural chemical compositions, and the agricultural chemical compositions or formulations of agricultural chemicals, to be used in the preparation of the agricultural chemical compositions (1) and (2) of the present invention will be described, though it is to be understood that the present invention is not restricted thereto.

Examples of Bactericides, that is, the active ingredients used for bactericide compositions and commercially available bactericide compositions, include Dipher (zinc ethylenebisdithiocarbamate) mfd. by Sankyo Co., Ltd., Maneb-dithane (manganese ethylenebisdithiocarbamate) mfd. by Sankyo Co., Ltd., Thiuram 80 [bis(dimethylthiocarbamoyl) disulfide] mfd. by Sankyo Co., Ltd., Manzeb (zinc/manganese ethylenebisdithiocarbamate) mfd. by Tokyo Organic Chemical Industries Co., Ltd., Bis-dithane (bisdimethyldithiocarbamoyl zinc ethylenebisdithiocarbamate) mfd. by Sankyo Co., Ltd., Antracol (zinc propylenebisdithiocarbamate) mfd. by Nihon Bayer Agrochen K.K., benzimidazole bactericides such as Benlate [methyl 1-(butylcarbamoyl)-2-benzimidazolecarbamate] mfd. by Sankyo Co., Ltd. and Thopsin M [1,2-bis(3-methoxycarbonyl-2-thioureido)benzene] mfd. by Nippon Soda K.K., Ronilan [3-(3,5-dichlorophenyl)-5-methyl-5-vinyl-1,3-oxazolidine-2,4-dione] mfd. by Sankyo Co., Ltd., Rovral [3-(3,5-dichlorophenyl)-N-isopropyl-2,4-dioxoimidazolidine-1-carboxamide] mfd. by Shionogi Pharmaceutical Co., Ltd., Sumilex [N-(3,5-dichlorophenyl)-1,2-dimethylcyclopropane-1,2-dicarboximide] mfd. by Sumitomo Chemical Co., Ltd., Triazine [2,4-dichloro-6-(2-chloroanilino)-1,3,5-triazine] mfd. by Nippon Soda K.K., Trifmine [(E)-4-chloro-α,α,α-trifluoro-N-(1-imidazol-1-yl-2-propoxyethylidene-o-toluidine] mfd. by Nippon Soda K.K., Ridomil [methyl N-(2-methoxyacetyl)-N-(2,6-xylyl)-D,L-alaninate] mfd. by Sankyo Co., Ltd., Baycoral [all-rac-1-(biphenyl-4-yloxy)-3,3-dimethyl-1-(1H-1,2,4-triazol-1-yl)-2-butan-2-ol] mfd. by Nihon Bayer Agrochen K.K., Bayleton [1-(4-chlorophenoxy)-3,3-dimethyl-1-(1,2,4-triazol-1-yl)-2-butanone] mfd. by Nihon Bayer Agrochen K.K., Fuji-One (diisopropyl 1,3-dithiolan-2-ylidenemalonate) mfd. by Nihon Nouyaku K.K., Daconil (tetrachloroisophthalonitrile) mfd. by Kumiai Chemical K.K., Pansoil (5-ethoxy-3-trichloromethyl-1,2,4-thiadiazole) mfd. by Sankyo Co., Ltd., Rabcide (4,5,6,7-tetrachlorophthalide) mfd. by Sankyo Co., Ltd., Kitazin P (O,O-diisopropyl-S-benzyl thiophosphate) mfd. by Kumiai Chemical K.K., Hinosan (O-ethyl-S,S-diphenyl dithiophosphate) mfd. by Sankyo Co., Ltd., Oryzemate (3-allyloxy-1,2-benzisothiazole 1,1-dioxide) mfd. by Meiji Seika Co., Ltd., Orthocide (N-trichloromethylthio-tetrahydro-phthalimide) mfd. by Sankyo Co., Ltd., Rally and Pozicklor.

In the case of insecticides, they include pyrethroid insecticides such as Fenvalerate [α-cyano-3-phenoxybenzyl-2-(4-chlorophenyl)-3-methylvalerate], e.g., Vegiphon mfd. by Sankyo Co., Ltd., and Baytroid [cyano-4-fluoro-3-phenoxyphenylmethyl 3-(2,2-dichloroethenyl)-2,2-dimethylcyclopropanecarboxylate] mfd. by Nihon Bayer Argochen K.K., organophosphorus insecticides such as DDVP (2,2-dichlorovinyl dimethyl phosphate), e.g., Des mfd. by Sankyo Co., Ltd., Sumithion (O,O-dimethyl-O-(3-methyl-4-nitrophenyl)-thiophosphate) mfd. by Sumitomo Chemical Co.; Ltd., Malathion (S-[1,2-bis(ethoxycarbonyl)ethyl] dimethyl phosphorothiolthionate) mfd. by Sankyo Co., Ltd., Dimethoate [dimethyl S-(N-methylcarbamoylmethyl) dithiophosphate] mfd. by Sankyo Co., Ltd., Papthion (S-[α-(ethoxycarbonyl)benzyl] dimethyl phosphorothiolthionate) mfd. by Sankyo Co., Ltd., and Baycid [O,O-dimethyl 0-(3-methyl-4-methylthiophenyl)-thiophosphate], carbamate insecticides such as Bassa (o-butylphenyl methylcarbamate) mfd. by Sankyo Co., Ltd., Tsumacide (m-tolyl methylcarbamate) mfd. by Sankyo Co., Ltd., Meobal (3,4-dimethylphenyl N-methylcarbamate) mfd. by Sankyo Co., Ltd., and Papnac (1-naphthyl N-methylcarbamate) mfd. by Sankyo Co., Ltd., and Lannate (S-methyl-N-[(methylcarbamoyl)-oxy]thioacetoimide) mfd. by Sankyo Co., Ltd., and Padan [1,3-bis(carbamoylthio)-2-(N,N-dimethylamino)-propane hydrochloride] mfd. by Takeda K.K.

In the case of miticides, they include Acricid (2,4-dinitro-6-sec-butylphenyl dimethylacrylate) mfd. by Sankyo Co., Ltd., Akar (ethyl 4,4-dichlorobenzilate) mfd. by Sankyo Co., Ltd., Kelthane [1,1-bis(p-chlorophenyl)-2,2,2-trichloroethanol] mfd. by Sankyo Co., Ltd., Omite [2-(p-tert-butylphenoxy)-cyclohexyl 2-propinyl sulfite] mfd. by Uniroyal Chemical Co., Ltd., Osadan [hexakis(β,β-dimethylphenethyl)distannoxane] mfd. by Shell Chemical Co., Ltd., Nissorun [trans-5-(4-chlorophenyl)-N-cyclohexyl-4-methyl-2-oxothiazolidine-3-carboxamide] mfd. by Nippon Soda K.K., Dani-Cut [3-methyl-1,5-bis(2,4-xylyl)-1,3,5-triazapenta-1,4-diene) mfd. by Nissan Chemical Co., Ltd., Tetradifon (2,4,5,4'-tetrachloro-diphenyl sulfone), Sunmite, Milveknock and Danitron.

In the case of herbicides, they include Stam (3,4-dichloropropionanilide) mfd. by Sankyo Co., Ltd, Saturn [S-(4-chlorobenzyl) N,N-diethylthiolcarbamate] mfd. by Kumiai Chemical K.K., Roundup [N-(phosphonomethyl)glycine isorpopylamine salt] mfd. by Monsant, Karmex [3-(3,4-dichlorophenyl)-1,1-dimethylurea] mfd. by Tomono Agrichemical K.K., Paraquat (1,1-dimethyl-4,4'-dipyridinium dichloride) mfd. by Nihon Agrichemical K.K., Basta [ammonium DL-homoalanin-4-yl-(methyl)phosphinate] mfd. by Ishihara K.K., Herbace (sodium salt of L-2-amino-4-[(hydroxy)(methyl)-phosphinoyl ]butylyl-L-alanyl-L-alanine) mfd. by Meiji Seika Co. Ltd., Lasso [2-chloro-2',6'-diethyl-N-(methoxyethyl)acetanilide] and VASTA.

In the case of plant growth regulators, they include MH (maleic hydrazide), Ethrel (2-chloroethylphosphonic acid), UASTA and Bialaphos.

The agricultural chemical compositions (1) and (2) of the present invention may further contain one or more plant growth regulators other than those cited above, fertilizers and preservatives.

The agricultural chemical compositions (1) and (2) according to the present invention may contain all components and may be used as it is or after dilution. Alternately, the agricultural chemical compositions (1) and (2) may be prepared before using by blending or mixing an agricultural chemical composition free from the above-described adjuvant(s) with the above-described adjuvant(s), and it may be used as it is or after dilution. The potentiating effect due to the above-described adjuvant(s) according to the present invention can be achieved in either case.

The kit (1) according to the present invention, which comprises package (A) comprising the mixture of compounds represented by the above general formula (I) which has n of from 2 to 50 on the average and x1+y1+z1+x2+y2+z2+x3+y3+z3 of from 0 to 100 on the average and package (B) comprising an agricultural chemical, is used for the preparation of the agricultural chemical composition (1).

The kit (2) according to the present invention, which comprises package (A) comprising the mixture of compounds represented by the above general formula (I) which has n of from 2 to 50 on the average and x1+y1+z1+x2+y2+z2+x3+y3+z3 of from 0 to 100 on the average, package (C) comprising a surfactant other than the compounds represented by the above general formula (I) and package (B) comprising an agricultural chemical, and the kit (3) according to the present invention, which comprises package (D) comprising the mixture of compounds represented by the above general formula (I) which has n of from 2 to 50 on the average and x1+y1+z1+x2+y2+z2+x3+y3+z3 of from 0 to 100 on the average and a surfactant other than the compounds represented by the above general formula (I) and package (B) comprising an agricultural chemical, are used for the preparation of the agricultural chemical composition (2).

For package (B), a package comprising a commercially available agricultural chemical composition (a), that is, a commercially available agricultural chemical formulation may be employed.

In the present invention, an agricultural chemical compositions (3) and (4), each of which contains from 0.02 to 8% by weight of the adjuvant(s) according to the present invention and an agricultural chemical which is present in an amount of 0.1 to 50 times as much as the adjuvant(s), are used in order to achieve bactericidal, insecticidal, miticidal, herbicidal or plant growth regulating effects. The agricultural chemical compositions (3) and (4) are generally prepared by diluting the agricultural chemical compositions (1) and (2), respectively. Examples:

To further illustrate the present invention in greater detail, and not by way of limitation, the following Examples are given.

Production Example 1

441 g of a mixture of polyglycerols (average molecular weight: 500, manufactured by Sakamoto Yakuhin K.K.), 282 g of stearic acid and 0.7 g of NaOH were fed into a reactor. After replacing the atmosphere in the system with $N_2$, the mixture was heated to 100° C. and stirred. After 2 hours, the mixture was further heated to 240° C. and then maintained at this temperature for 5 hours (distillate in the system: 120 g). A sampling analysis indicated that the saponification value of the reaction mixture was 85 while the hue thereof was G (Gardner color scale) 6 or below. Then the mixture was cooled and the moisture was removed by filtration (corresponding to the adjuvant 5).

EXAMPLE 1

The adjuvants according to the present invention and comparative ones, as listed in Tables 1 and 2, and the marketed herbicide compositions, namely, Karmex wettable powder, Herbiace water-soluble powder and Roundup solution were employed for the evaluation of the herbicidal effect. Each of the adjuvants and each of the marketed herbicide compositions were dissolved in city water in such a manner as to give a concentration of 0.2% by weight and a dilution ratio of 300-fold, respectively. Then 10 ml/pot of each of the agricultural chemical compositions thus prepared was applied to crabgrass (a woody herb), which had been uniformly grown, to evaluate the herbicidal effect.

In the case where no adjuvant was added (free from any adjuvant), the same procedure was conducted.

The crabgrass plants were grown to the tri- or tetrafoliate stage to a height of about 10 cm. Each pot had 25 plants.

The herbicidal rate (%) was expressed as a ratio of the fresh weight of the above-ground part measured 10 days after the application to that of the control (untreated) lot [refer to formula (III)].

Formula (III):

$$\text{herbicidal effect} = \frac{(\text{above-ground part fresh weight of control lot}) - (\text{above-ground part fresh weight of test lot})}{(\text{above-ground part fresh weight of control lot})} \times 100(\%)$$

Tables 1 and 2 summarize the results.

TABLE 1

| | | | Herbicidal rate (%) | | |
| --- | --- | --- | --- | --- | --- |
| | No. | Adjuvant | Karmex wettable powder | Herbiace water-soluble powder | Roundup solution |
| Invention composition | 1 | diglycerol monostearate | 89.4 | 100.0 | 100.0 |
| | 2 | tetraglycerol monostearate | 89.3 | 100.0 | 100.0 |
| | 3 | hexaglycerol monomyristate | 84.3 | 97.4 | 100.0 |
| | 4 | hexaglycerol monooleate | 85.4 | 96.3 | 98.7 |

TABLE 1-continued

|  |  | Herbicidal rate (%) | | |
| --- | --- | --- | --- | --- |
| No. | Adjuvant | Karmex wettable powder | Herbiace water-soluble powder | Roundup solution |
| 5 | hexaglycerol monostearate | 87.9 | 100.0 | 100.0 |
| 6 | decaglycerol monolaurate | 90.4 | 10.00 | 100.0 |
| 7 | decaglycerol monomyristate | 91.3 | 96.5 | 98.4 |
| 8 | decaglycerol monooleate | 97.4 | 89.4 | 100.0 |
| 9 | decaglycerol monostearate | 99.4 | 100.0 | 100.0 |
| 10 | decaglycerol pentastearate | 100.0 | 100.0 | 100.0 |
| 11 | diglycerol monoricinoleate | 100.0 | 100.0 | 100.0 |
| 12 | tetraglycerol diricinoleate | 100.0 | 100.0 | 100.0 |
| 13 | tetraglycerol monooleate monosulfate/triethanolamine | 87.9 | 98.4 | 98.4 |

TABLE 2

|  |  |  | Herbicidal rate (%) | | |
| --- | --- | --- | --- | --- | --- |
|  | No. | Adjuvant | Karmex wettable powder | Herbiace water-soluble powder | Roundup solution |
| Invention composition | 14 | hexaglycerol monoricinoleate | 100.0 | 100.0 | 100.0 |
|  | 15 | diglycerol monostearate/Emulgen 909*1: 80/20 | 90.1 | 98.8 | 96.5 |
|  | 16 | decaglycerol monooleate/Emunon 4110*2: 80/20 | 83.5 | 94.2 | 99.8 |
|  | 17 | triglycerol POP(8)/Emulgen 103*3: 80/20 | 94.2 | 99.8 | 100.0 |
|  | 18 | triglycerol distearate/Rheodol TWO-120*4: 60/40 | 98.0 | 96.6 | 100.0 |
|  | 19 | diglycerol/glycerol: 50/50 | 90.3 | 95.5 | 90.2 |
| Comparative composition | 20 | glycerol | 31.4 | 80.0 | 72.3 |
|  | 21 | glycerol monolaurate | 49.5 | 69.5 | 74.4 |
|  | 22 | glycerol monostearate | 30.5 | 68.8 | 69.8 |
|  | 23 | glycerol dilaurate | 35.2 | 70.0 | 70.2 |
|  | 24 | none | 18.4 | 67.5 | 68.5 |

Note
*1: Emulgen 909; POE(9) nonylphenyl ether, mfd. by Kao Corporation.
*2: Emunon 4110; POE (10) $C_{17}H_{35}COOH$, mfd. by Kao Corporation.
*3: Emulgen 103; POE(10) $C_{12}H_{25}OH$, mfd. by Kao Corporation.
*4: Rheodol TWO-120; sorbitan ester of POE(20) $C_{17}H_{33}COOH$, mfd. by Kao Corporation.

Others-1

The compounds employed in the invention compositions as the adjuvants are each a mixture. The degree of polymerization of the polyglycerol part in the compound means an average degree of polymerization of the mixture, and the number of ester group(s) in the compound means an average value of the mixture.

Others-2

POE and POP means polyoxyethylene and polyoxypropylene, respectively. The compounds having POE or POP are provided as mixtures and each number in the parentheses shows the average of the total number of moles of oxyalkylene in the molecule.

Others-3

When two mixtures or a mixture and a compound are used together as the adjuvants (invention compositions 15 to 19), the ratio given above is by weight.

The matters described above are applied similarly hereinafter.

EXAMPLE 2

Rice insect larvae of the third instar were incubated to evaluate the effect of each insecticide by the dipping method (three runs, each lot having 10 larvae). That is, the rice insect larvae were transplanted onto a kidney bean leaf disc (each lot having 30 insects, three runs) and incubated at 25° C. for 24 hours. Then the whole leaf disc was immersed in a test solution for 5 seconds. After allowing to stand at 25° C. for 48 hours, the disc was observed to determine the insecticidal rate based on the control lot (refer to the method employed for determining the herbicidal rates).

Each of the adjuvants as listed in Table 3 was dissolved in a diluted marketed insecticide compositions, namely, a diluted solution (dilution ratio of 2,000-fold) of Sumithion emulsion (active ingredient: 50% by weight) or a diluted solution (dilution ratio of 2,000-fold) of Malathion emulsion (active ingredient: 50% by weight), in such a manner as to give a concentration of 0.1% by weight.

In the case where no adjuvant was added (free from any adjuvant), the same procedure was conducted.

Table 3 summarizes the results.

TABLE 3

|  |  |  | Insecticidal rate (%) | |
| --- | --- | --- | --- | --- |
|  | No. | Adjuvant | Sumithion emulsion | Malathion emulsion |
| Invention composition | 1 | diglycerol monostearate | 90.0 | 100.0 |
|  | 2 | diglycerol monolaurate | 100.0 | 90.3 |

TABLE 3-continued

|  | No. | Adjuvant | Insecticidal rate (%) Sumithion emulsion | Insecticidal rate (%) Malathion emulsion |
|---|---|---|---|---|
|  | 3 | diglycerol monolaurate POE(3) | 79.3 | 100.0 |
|  | 4 | triglycerol monostearate | 97.5 | 76.4 |
|  | 5 | triglycerol monopalmitate | 100.0 | 90.4 |
|  | 6 | tetraglycerol monolaurate | 95.4 | 94.5 |
|  | 7 | decaglycerol monostearate | 100.0 | 98.2 |
|  | 8 | diglycerol distearate | 98.3 | 100.0 |
|  | 9 | diglycerol dilaurate | 100.0 | 100.0 |
|  | 10 | triglycerol distearate/ triglycerol dipalmitate: 30/70 | 100.0 | 97.2 |
|  | 11 | diglycerol | 100.0 | 100.0 |
|  | 12 | triglycerol | 82.4 | 89.4 |
|  | 13 | tetraglycerol/decaglycerol: 50/50 | 100.0 | 99.4 |
|  | 14 | triglycerol POE (8)/ tetraglycerol POE (20): 10/90 | 88.4 | 80.4 |
|  | 15 | decaglycerol POE (20) | 76.8 | 96.5 |
|  | 16 | diglycerol POP (3)/ triglycerol POP (5): 50/50 | 89.5 | 98.8 |
|  | 17 | diglycerol dilaurate/ Rheodol TWO-120: 80/20 | 94.5 | 93.3 |
|  | 18 | triglycerol POP (5)/Emulgen 909: 80/20 | 100.0 | 89.9 |
|  | 19 | sodium hexaglycerol monopalmitate monosulfate | 89.4 | 87.4 |
|  | 20 | sodium hexaglycerol monopalmitate monosulfate/ Emulgen 909: 80/20 | 95.4 | 99.4 |
| Comparative composition | 21 | glycerol | 50.0 | 54.2 |
|  | 22 | glycerol monolaurate | 50.4 | 55.0 |
|  | 23 | glycerol distearate | 60.5 | 54.0 |
|  | 24 | glycerol monopalmitate | 55.3 | 60.3 |
|  | 25 | none | 48.8 | 52.3 |

EXAMPLE 3

Female *Tetranychus kanzawai* imagines were transplanted onto a kidney bean leaf disc (each lot having 30 insects, three runs) and incubated at 25° C. for 24 hours. Then the whole leaf disc was immersed in a test solution for 5 seconds. After allowing to stand at 25° C. for 48 hours, the disc was observed to determine the insecticidal rate based on the control lot (refer to the method employed for determining the herbicidal rates). As miticide compositions, Nissolan V emulsion (active ingredient: 55% by weight) and Osadan wettable powder (active ingredient: 15% by weight), each diluted 2,000-fold, were used. Each of the adjuvants, as listed in Table 4, was added to each of the diluted solutions in such a manner as to give a concentration of 0.1%. Table 4 shows the results.

In the case where no adjuvant was added to each of the diluted solutions (free from any adjuvant), the same procedure was conducted.

For comparison, each of adjuvants free from any agricultural chemicals, namely, each of diglycerol monostearate, decaglycerol, decaglycerol dilaurate, triglycerol monolaurate POP(5) and triglycerol POE(8), was dissolved in city water in such a manner as to give a concentration of 0.2% by weight and each of the solutions thus obtained was subjected to the same test as the one described above. As a result, each of these solutions gave a miticidal ratio of 0%.

TABLE 4

|  | No. | Adjuvant | Insecticidal rate (%) Nissolan V emulsion | Insecticidal rate (%) Osadan wettable powder |
|---|---|---|---|---|
| Invention composition | 1 | diglycerol | 100.0 | 100.0 |
|  | 2 | tetraglycerol | 100.0 | 99.8 |
|  | 3 | hexaglycerol | 99.5 | 100.0 |
|  | 4 | decaglycerol | 100.0 | 100.0 |
|  | 5 | triglycerol POE(8) | 100.0 | 100.0 |
|  | 6 | triglycerol POE(18) | 98.8 | 98.5 |
|  | 7 | diglycerol monolaurate | 100.0 | 99.5 |
|  | 8 | diglycerol monostearate | 100.0 | 100.0 |
|  | 9 | triglycerol dilaurate | 100.0 | 100.0 |
|  | 10 | triglycerol tristearate | 100.0 | 100.0 |
|  | 11 | decaglycerol monolaurate | 100.0 | 100.0 |
|  | 12 | decaglycerol dilaurate | 99.8 | 98.5 |
|  | 13 | diglycerol monolaurate POE(3) | 100.0 | 99.5 |
|  | 14 | diglycerol distearate POE(10) | 98.9 | 80.4 |
|  | 15 | tetraglycerol distearate POP(8) | 100.0 | 100.0 |
|  | 16 | decaglycerol monolaurate POP(12) | 100.0 | 100.0 |
| Comparative composition | 17 | glycerol | 52.6 | 50.0 |
|  | 18 | glycerol monolaurate | 54.5 | 50.3 |
|  | 19 | glycerol distearate | 52.9 | 48.8 |
|  | 20 | glycerol monopalmitate | 57.4 | 54.3 |
|  | 21 | none | 52.4 | 43.2 |

As the above Examples 1 to 3 clearly show, the adjuvants according to the present invention were much superior to common surfactants in potentiating effect of insecticidal effect and thus usable in practice. On the other hand, the comparative adjuvants were not applicable to practical use, though they somewhat potentiated the effect of agricultural chemicals.

EXAMPLE 4

The test described in the above Example 1 was repeated except that Roundup emulsion and diglycerol monolaurate were employed, each in the amount specified in Table 5, respectively as a herbicide composition and as an adjuvant. Table 5 shows the results.

TABLE 5

| Test No. | Content of agricultural chemical (ppm) | Content of adjuvant (ppm) | Agr. chemical/ adjuvant ratio (by weight) | Herbicidal rate (%) |
|---|---|---|---|---|
| 1 | 2000 | 200 | 1/0.1 | 85.1 |
| 2 | 2000 | 1000 | 1/0.5 | 98.5 |
| 3 | 2000 | 2000 | 1/1.0 | 99.0 |
| 4 | 2000 | 10000 | 1/5 | 100 |
| 5 | 2000 | 24000 | 1/12 | 100 |
| 6 | 2000 | 30000 | 1/15 | 100 |
| 7 | 2000 | 36000 | 1/18 | 100 |
| 8 | 2000 | 0 | — | 30.4 |
| 9 | 0 | 0 | — | 0.0 |

EXAMPLE 5

The test described in the above Example 1 was repeated except that Roundup emulsion and decaglycerol distearate were employed, each in the amount specified in Table 6, respectively as a herbicide composition and as an adjuvant. Table 6 shows the results.

TABLE 6

| Test No. | Content of agricultural chemical (ppm) | Content of adjuvant (ppm) | Agr. chemical/ adjuvant ratio (by weight) | Herbicidal rate (%) |
| --- | --- | --- | --- | --- |
| 1 | 2000 | 200 | 1/0.1 | 88.1 |
| 2 | 2000 | 1000 | 1/0.5 | 97.5 |
| 3 | 2000 | 2000 | 1/1.0 | 100 |
| 4 | 2000 | 10000 | 1/5 | 100 |
| 5 | 2000 | 24000 | 1/12 | 100 |
| 6 | 2000 | 30000 | 1/15 | 100 |
| 7 | 2000 | 36000 | 1/18 | 100 |
| 8 | 2000 | 0 | — | 30.4 |
| 9 | 0 | 0 | — | 0.0 |

EXAMPLE 6

The test described in the above Example 1 was repeated except that Roundup emulsion and diglycerol monostearate POE(8) were employed, each in the amount specified in Table 7, respectively as a herbicide composition and as an adjuvant. Table 7 shows the results.

TABLE 7

| Test No. | Content of agricultural chemical (ppm) | Content of adjuvant (ppm) | Agr. chemical/ adjuvant ratio (by weight) | Herbicidal rate (%) |
| --- | --- | --- | --- | --- |
| 1 | 2000 | 200 | 1/0.1 | 94.5 |
| 2 | 2000 | 1000 | 1/0.5 | 99.5 |
| 3 | 2000 | 2000 | 1/1.0 | 100 |
| 4 | 2000 | 10000 | 1/5 | 100 |
| 5 | 2000 | 24000 | 1/12 | 100 |
| 6 | 2000 | 30000 | 1/15 | 100 |
| 7 | 2000 | 36000 | 1/18 | 100 |
| 8 | 2000 | 0 | — | 30.4 |
| 9 | 0 | 0 | — | 0.0 |

EXAMPLE 7

The test described in the above Example 2 was repeated except that Sumithion emulsion and triglycerol monopalmitate were employed, each in the amount specified in Table 8, respectively as an insecticide composition and as an adjuvant. Table 8 shows the results.

TABLE 8

| Test No. | Content of agricultural chemical (ppm) | Content of adjuvant (ppm) | Agr. chemical/ adjuvant ratio (by weight) | Insecticidal rate (%) |
| --- | --- | --- | --- | --- |
| 1 | 250 | 25 | 1/0.1 | 63.5 |
| 2 | 250 | 125 | 1/0.5 | 74.2 |
| 3 | 250 | 250 | 1/1.0 | 78.6 |
| 4 | 250 | 500 | 1/2.0 | 100 |
| 5 | 250 | 1000 | 1/4.0 | 100 |
| 6 | 250 | 2500 | 1/10 | 100 |
| 7 | 250 | 5000 | 1/20 | 100 |
| 8 | 250 | 0 | — | 51.2 |
| 9 | 0 | 0 | — | 0.0 |

EXAMPLE 8

The test described in the above Example 3 was repeated except that Osadan wettable powder and decaglycerol monolaurate POP(15) were employed, each in the amount specified in Table 9, respectively as a miticide composition and as an adjuvant. Table 9 shows the results.

TABLE 9

| Test No. | Content of agricultural chemical (ppm) | Content of adjuvant (ppm) | Agr. chemical/ adjuvant ratio (by weight) | Miticidal rate (%) |
| --- | --- | --- | --- | --- |
| 1 | 100 | 10 | 1/0.1 | 75.4 |
| 2 | 100 | 50 | 1/0.5 | 94.3 |
| 3 | 100 | 100 | 1/1.0 | 100 |
| 4 | 100 | 200 | 1/2.0 | 100 |
| 5 | 100 | 1000 | 1/10 | 100 |
| 6 | 100 | 1500 | 1/15 | 100 |
| 7 | 100 | 2000 | 1/20 | 100 |
| 8 | 100 | 0 | — | 48.0 |
| 9 | 0 | 0 | — | 0.0 |

EXAMPLE 9

The test described in the above Example 3 was repeated except that Osadan wettable powder and triglycerol distearate POE(20) were employed, each in the amount specified in Table 10, respectively as a miticide composition and as an adjuvant. Table 10 shows the results.

TABLE 10

| Test No. | Content of agricultural chemical (ppm) | Content of adjuvant (ppm) | Agr. chemical/ adjuvant ratio (by weight) | Miticidal rate (%) |
| --- | --- | --- | --- | --- |
| 1 | 100 | 10 | 1/0.1 | 56.8 |
| 2 | 100 | 50 | 1/0.5 | 84.5 |
| 3 | 100 | 100 | 1/1.0 | 89.9 |
| 4 | 100 | 200 | 1/2.0 | 100 |
| 5 | 100 | 1000 | 1/10 | 100 |
| 6 | 100 | 1500 | 1/15 | 100 |
| 7 | 100 | 2000 | 1/20 | 100 |
| 8 | 100 | 0 | — | 48.0 |
| 9 | 0 | 0 | — | 0.0 |

EXAMPLE 10

The test described in the above Example 1 was repeated except that Herbiace water-soluble powder and tetraglycerol distearate were employed, each in the amount specified in Table 11, respectively as a herbicide composition and as an adjuvant. Table 11 shows the results.

TABLE 11

| Test No. | Content of agricultural chemical (ppm) | Content of adjuvant (ppm) | Agr. chemical/ adjuvant ratio (by weight) | Herbicidal rate (%) |
| --- | --- | --- | --- | --- |
| 1 | 2000 | 100 | 1/0.05 | 70.2 |
| 2 | 2000 | 200 | 1/0.1 | 88.5 |
| 3 | 2000 | 500 | 1/0.25 | 100.0 |
| 4 | 1000 | 50 | 1/0.05 | 41.2 |
| 5 | 1000 | 100 | 1/0.1 | 100.0 |
| 6 | 1000 | 200 | 1/0.2 | 100.0 |
| 7 | 1000 | 1000 | 1/1 | 100.0 |
| 8 | 500 | 2500 | 1/5 | 54.3 |
| 9 | 500 | 7500 | 1/15 | 70.4 |
| 10 | 2000 | 0 | — | 68.3 |

TABLE 11-continued

| Test No. | Content of agricultural chemical (ppm) | Content of adjuvant (ppm) | Agr. chemical/ adjuvant ratio (by weight) | Herbicidal rate (%) |
|---|---|---|---|---|
| 11 | 1000 | 0 | — | 40.5 |
| 12 | 500 | 0 | — | 30.1 |

As Table 11 clearly shows, the herbicidal rate can be elevated by increasing the content of the adjuvant, even when a small amount of the agricultural chemical is employed.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What we claimed is:

1. An agricultural chemical composition (2) comprising a mixture of compounds represented by the following general formula (I) which has n of from 2 to 50 on the average and x1+y1+z1+x2+y2+z2+x3+y3+z3 of from 0 to 100 on the average; and a nonionic surfactant selected from the group consisting of polyoxyethylene alkyl ethers, polyoxyethylene alkylaryl ethers, polyoxyethylene alkylaryl ether/formaldahyde condensates, polyoxyalkylene aryl ethers, polyoxyalkylene alkyl esters, polyoxyalkylene alkyl sorbitol esters, polyoxyalkylene sorbitan esters, polyoxyalkylene alkyl glycerol esters, polyoxyalkylene block copolymers, polyoxyalkylene block copolymer alkylglycerol esters, polyoxyalkylene alkyl sulfonamides, polyoxyalkylene rosin esters, polyoxypropylene block copolymers, polyoxyethylene oleyl ethers and polyoxyalkylene alkylphenols, and mixtures thereof, as the adjuvants; and an agricultural chemical, wherein the weight ratio of the total amount of the adjuvants to the agricultural chemical ranges from 0.1 to 20, wherein the weight ratio of the mixture of compounds represented by the general formula (I) to the said nonionic surfactant ranges from 90:10 to 60:40:

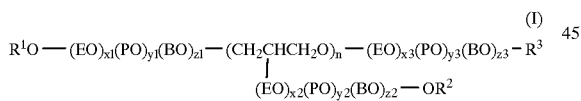

(I)

wherein $R_1$, $R^2$ and $R^3$ each represent a hydrogen atom or an acyl group having from 2 to 31 carbon atoms, $-SO_3Na$, $-SO_3K$, $-SO_3H.N(C_2H_4OH)_3$ or $-SO_3H.NH(C_2H_4OH)_2$;

$(EO)_{x1}$, $(EO)_{x2}$ and $(EO)_{x3}$ each represent a polyoxyethylene chain; $(PO)_{x1}$, $(PO)_{x2}$ and $(PO)_{x3}$ each represent a polyoxypropylene chain; $(BO)_{x1}$, $(BO)_{x2}$ and $(BO)_{x3}$ each represent a polyoxybutylene chain;

n represents an integer of 1 or more; x1, y1, z1, x2, y2, z2, x3, y3 and z3 each represent 0 or an integer of 1 or more; x1+y1+z1, x2+y2+z2 and x3+y3+z3 each represent 0 or an integer of 1 to 200; and x1+y1+z1+x2+y2+z2+x3+y3+z3 represents 0 or an integer of 1 to 600.

2. The agricultural chemical composition according to claim 1 wherein said nonionic surfactant is selected from the group consisting of a polyoxyalkylene alkyl sorbitol ester, a polyoxyalkylene alkyl ester, a polyoxyalkylene sorbitan ester, and a polyoxyalkylene alkyl glycerol ester.

3. A method for potentiating the effectiveness of an agricultural chemical which comprising applying an agricultural chemical composition according to claim 2 to a locus which would benefit from such treatment.

4. The agricultural chemical composition (2) as claimed in claim 1, wherein the mixture is mixture (a) of compounds represented by the general formula (I) which has n of from 2 to 50 on the average and x1+y1+z1+x2+y2+z2+x3+y3+z3 of from 1 to 100 on the average, or mixture (b) of compounds represented by the following general formula (I') which has n of from 2 to 50 on the average:

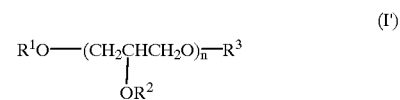

(I')

wherein $R^1$, $R^2$ and $R^3$ each represent a hydrogen atom, an acyl group having from 2 to 31 carbon atoms, $-SO_3Na$, $-SO_3K$, $-SO_3H.N(C_2H_4OH)_3$ or $-SO_3H.NH(C_2H_4OH)_2$ provided that at least one of $R^1$, $R^2$ and $R^3$ represent an acyl group having from 2 to 31 carbon atoms, $-SO_3Na$, $-SO_3K$, $-SO_3H.N(C_2H_4OH)_3$ or $-SO_3H.NH(C_2H_4OH)_2$; and n represents an integer of 1 or more.

5. The agricultural chemical composition (2) as claimed in claim 1, wherein the mixture has n of from 2 to 10 on the average.

6. The agricultural chemical composition (2) as claimed in claim 1, wherein the agricultural chemical is selected from the group consisting of active ingredients of bactericides, insecticides, miticides, herbicides and plant growth regulators.

7. The agricultural chemical composition (2) as claimed in claim 1, wherein the weight ratio of the total amount of the adjuvants to the agricultural chemical ranges from 0.1 to 10.

8. The agricultural chemical composition (2) as claimed in claim 1, wherein the weight ratio of the mixture of compounds represented by the general formula (I) to the surfactant other than the compounds represented by the general formula (I) ranges from 90:10 to 60:40.

9. A herbicidal composition comprising:

(A) a mixture of compounds represented by the following general formula (I):

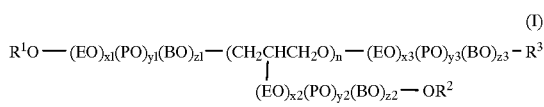

(I)

wherein $R^1$, $R^2$ and $R^3$ each represent a hydrogen atom, an acyl group having from 2 to 31 carbon atoms, $-SO_3Na$, $-SO_3K$, $-SO_3H.N(C_2H_4OH)_3$ or $-SO_3H.NH(C_2H_4OH)_2$, provided that at least one of $R^1$, $R^2$ and $R^3$ represents an acyl group having from 2 to 31 carbon atoms;

$(EO)_{x1}$, $(EO)_{x2}$ and $(EO)_{x3}$ each represent a polyoxyethylene chain;

$(PO)_{y1}$, $(PO)_{y2}$ and $(PO)_{y3}$ each represent a polyoxypropylene chain;

$(BO)_{z1}$, $(BO)_{z2}$, and $(BO)_{z3}$ each represent a polyoxybutylene chain;

wherein n represents an integer of 1 or more and in said mixture of compounds of formula (I) n is from 2 to 50 on the average;

x1, y1, z1, x2, y2, z2, x3, y3 and z3 each represent 0 or an integer of 1 or more;

the sums of x1+y1+z1, x2+y2+z2 and x3+y3+z3 each represent 0 or an integer of 1 to 200;

the sum of x1+y1+z1+x2+y2+z2+x3+y3+z3 represents 0 or an integer of 1 to 600 and in said mixture of compounds of formula (I), the sum of x1+y1+z1+x2+y2+z2+x3+y3+z3 is from 0 to 100 on the average;

(B) a suitable surfactant other than the compounds represented by general formula (I), selected from the group consisting of nonionic, anionic, cationic and amphoteric surfactants and mixtures thereof;

(C) a herbicidal chemical selected from the group consisting of 3,4-dichloropropionanilide, S-(4-chlorobenzyl)N,N-diethylthiolcarbamate, N-(phosphonomethyl)-glycine isopropylamine salt, 3-(3,4-dichlorophenyl)-1,1-dimethyl urea, 1,1-dimethyl-4,4'-dipyridinium dichloride, ammonium DL-homoalanin-4-yl-(methyl)phosphinate, the sodium salt of L-2-amino-4-[(hydroxy)(methyl)-phosphinateyl]butyl-L-alanyl-L-alanine and 2-chloro-2',6'-diethyl-N-(methoxyethyl)acetanilide, wherein the weight ratio of the mixture (A and B) to the herbicidal chemical (C) ranges from 0.1 to 20.

10. A kit (1) comprising package (A) comprising a mixture of compounds represented by the following general formula (I) which has n of from 2 to 50 on the average and x1+y1+z1+x2+y2+z2+x3+y3+z3 of from 0 to 100 on the average and package (B) comprising an agricultural chemical, wherein the weight ratio of the mixture to the agricultural chemical ranges from 0.1 to 20:

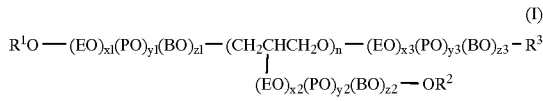

wherein $R^1$, $R^2$ and $R^3$ each represent a hydrogen atom or an acyl group having from 2 to 31 carbon atoms, —$SO_3Na$, —$SO_3K$, —$SO_3H.N(C_2H_4OH)_3$ or —$SO_3H.NH(C_2H_4OH)_2$;

$(EO)_{x1}$, $(EO)_{x2}$ and $(EO)_{x3}$ each represent a polyoxyethylene chain;

$(PO)_{y1}$, $(PO)_{y2}$ and $(PO)_{y3}$ each represent a polyoxypropylene chain;

$(BO)_{z1}$, $(BO)_{z2}$ and $(BO)_{z3}$ each represent a polyoxybutylene chain;

n represents an integer of 1 or more;

x1, y1, z1, x2, y2, z2, x3, y3 and z3 each represent 0 or an integer of 1 or more;

x1+y1+z1, x2+y2+z2 and x3+y3+z3 each represent 0 or an integer of 1 to 200; and x1+y1+z1+x2+y2+z2+x3+y3+z3 represents 0 or an integer of 1 to 600.

11. The kit (1) as claimed in claim 10, wherein the package (B) contains an agricultural chemical composition (a) containing an agricultural chemical in the form of an emulsion, a solution, a wettable powder, a granule, a dust or a flowable powder.

12. A kit (2) comprising package (A) comprising a mixture of compounds represented by the following general formula (I) which has n of from 2 to 50 on the average and x1+y1+z1+x2+y2+z2+x3+y3+z3 of from 0 to 100 on the average, package (C) comprising a surfactant other than the compounds represented by the following general formula (I) and package (B) comprising an agricultural chemical, wherein the weight ratio of the total amount of the mixture and the surfactant to the agricultural chemical ranges from 0.1 to 20:

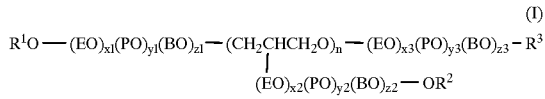

wherein $R^1$, $R^2$ and $R^3$ each represent a hydrogen atom or an acyl group having from 2 to 31 carbon atoms, —$SO_3Na$, —$SO_3K$, —$SO_3H.N(C_2H_4OH)_3$ or —$SO_3H.NH(C_2H_4OH)_2$;

$(EO)_{x1}$, $(EO)_{x2}$ and $(EO)_{x3}$ each represent a polyoxyethylene chain;

$(PO)_{y1}$, $(PO)_{y2}$ and $(PO)_{y3}$ each represent a polyoxypropylene chain;

$(BO)_{z1}$, $(BO)_{z2}$ and $(BO)_{z3}$ each represent a polyoxybutylene chain;

n represents an integer of 1 or more;

x1, y1, z1, x2, y2, z2, x3, y3 and z3 each represent 0 or an integer of 1 or more;

x1+y1+z1, x2+y2+z2 and x3+y3+z3 each represent 0 or an integer of 1 to 200; and x1+y1+z1+x2+y2+z2+x3+y3+z3 represents 0 or an integer of 1 to 600.

13. The kit (2) as claimed in claim 12 wherein the package (B) contains an agricultural chemical composition (a) containing an agricultural chemical in the form of an emulsion, a solution, a wettable powder, a granule, a dust or a flowable powder.

14. A kit (3) comprising package (D) comprising a mixture of compounds represented by the following general formula (I) which has n of from 2 to 50 on the average and x1+y1+z1+x2+y2+z2+x3+y3+z3 of from 0 to 100 on the average and a surfactant other than the compounds represented by the following general formula (I) and package (B) comprising an agricultural chemical, wherein the weight ratio of the total amount of the mixture and the surfactant to the agricultural chemical ranges from 0.1 to 20:

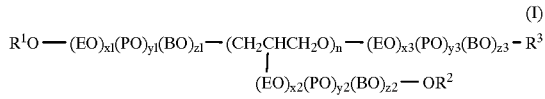

wherein $R^1$, $R^2$ and $R^3$ each represent a hydrogen atom or an acyl group having from 2 to 31 carbon atoms, —$SO_3Na$, —$SO_3K$, —$SO_3H.N(C_2H_4OH)_3$ or —$SO_3H.NH(C_2H_4OH)_2$;

$(EO)_{x1}$, $(EO)_{x2}$ and $(EO)_{x3}$ each represent a polyoxyethylene chain;

$(PO)_{y1}$, $(PO)_{y2}$ and $(PO)_{y3}$ each represent a polyoxypropylene chain;

$(BO)_{z1}$, $(BO)_{z2}$ and $(BO)_{z3}$ each represent a polyoxybutylene chain;

n represents an integer of 1 or more;

x1, y1, z1, x2, y2, z2, x3, y3 and z3 each represent 0 or an integer of 1 or more;

x1+y1+z1, x2+y2+z2 and x3+y3+z3 each represent 0 or an integer of 1 to 200; and x1+y1+z1+x2+y2+z2+x3+y3+z3 represents 0 or an integer of 1 to 600.

15. The kit (3) as claimed in claim 14, wherein the package (B) contains an agricultural chemical composition (a) containing an agricultural chemical in the form of an emulsion, a solution, a wettable powder, a granule, a dust or a flowable powder.

16. A bactericidal, insecticidal, miticidal, herbicidal or plant growth regulating method (1), wherein an agricultural chemical composition (3) comprising from 0.02 to 8% by weight of a mixture of compounds represented by the following general formula (I) which has n of from 2 to 50 on the average and x1+y1+z1+x2+y2+z2+x3+y3+z3 of from 0 to 100 on the average and an agricultural chemical which is present in an amount of from 0.1 to 50 times (by weight) as much as the mixture, is employed:

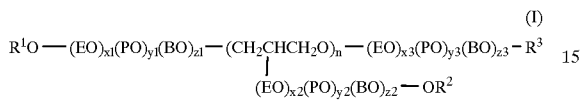

(I)

wherein $R^1$, $R^2$ and $R^3$ each represent a hydrogen atom or an acyl group having from 2 to 31 carbon atoms, $—SO_3Na$, $—SO_3K$, $—SO_3H \cdot N(C_2H_4OH)_3$ or $—SO_3H \cdot NH(C_2H_4OH)_2$;

$(EO)_{x1}$, $(EO)_{x2}$ and $(EO)_{x3}$ each represent a polyoxyethylene chain;

$(PO)_{y1}$, $(PO)_{y2}$ and $(PO)_{y3}$ each represent a polyoxypropylene chain;

$(BO)_{z1}$, $(BO)_{z2}$ and $(BO)_{z3}$ each represent a polyoxybutylene chain;

n represents an integer of 1 or more;

x1, y1, z1, x2, y2, z2, x3, y3 and z3 each represent 0 or an integer of 1 or more;

x1+y1+z1, x2+y2+z2 and x3+y3+z3 each represent 0 or an integer of 1 to 200; and x1+y1+z1+x2+y2+z2+x3+y3+z3 represents 0 or an integer of 1 to 600.

17. A bactericidal, insecticidal, miticidal, herbicidal or plant growth regulating method (2), wherein an agricultural chemical composition (4) comprising from 0.02 to 8% by weight of adjuvants comprising a mixture of compounds represented by the following general formula (I) which has n of from 2 to 50 on the average and x1+y1+z1+x2+y2+z2+x3+y3+z3 of from 0 to 100 on the average and a surfactant other than the compounds represented by the following general formula (I), and an agricultural chemical which is present in an amount of from 0.1 to 50 times (by weight) as much as the total amount of the adjuvants, is employed:

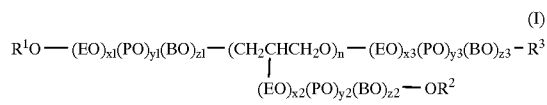

(I)

wherein $R^1$, $R^2$ and $R^3$ each represent a hydrogen atom or an acyl group having from 2 to 31 carbon atoms, $—SO_3Na$, $—SO_3K$, $—SO_3H \cdot N(C_2H_4OH)_3$ or $—SO_3H \cdot NH(C_2H_4OH)_2$;

$(EO)_{x1}$, $(EO)_{x2}$ and $(EO)_{x3}$ each represent a polyoxyethylene chain;

$(PO)_{y1}$, $(PO)_{y2}$ and $(PO)_{y3}$ each represent a polyoxypropylene chain;

$(BO)_{z1}$, $(BO)_{z2}$ and $(BO)_{z3}$ each represent a polyoxybutylene chain;

n represents an integer of 1 or more;

x1, y1, z1, x2, y2, z2, x3, y3 and z3 each represent 0 or an integer of 1 or more;

x1+y1+z1, x2+y2+z2 and x3+y3+z3 each represent 0 or an integer of 1 to 200; and x1+y1+z1+x2+y2+z2+x3+y3+z3 represents 0 or an integer of 1 to 600.

* * * * *